United States Patent [19]

Snelling

[11] 4,431,300

[45] Feb. 14, 1984

[54] AUTOMATIC DEVELOPABILITY SENSING IN ELECTROPHOTOGRAPHIC PRINTING

[75] Inventor: Christopher Snelling, Penfield, N.Y.

[73] Assignee: Xerox Corporation, Stamford, Conn.

[21] Appl. No.: 349,107

[22] Filed: Feb. 16, 1982

[51] Int. Cl.³ ............................................. G03G 15/08
[52] U.S. Cl. ............................ 355/14 D; 355/3 DD; 118/689; 118/690
[58] Field of Search .................... 355/3 DD, 14 D; 118/624, 644, 653, 657, 658, 665, 668, 688, 689, 690, 691; 430/120-123, 31, 30

[56] References Cited

U.S. PATENT DOCUMENTS

| | | | |
|---|---|---|---|
| 3,233,781 | 2/1966 | Grubbs | 355/14 D |
| 3,431,411 | 3/1969 | Harrick | 250/43.5 |
| 3,460,893 | 8/1969 | Wilks, Jr. | 356/96 |
| 3,591,287 | 7/1971 | Hannis | 356/51 |
| 3,727,065 | 4/1973 | Maksymiak | 118/691 X |
| 3,777,173 | 12/1973 | Landrith | 118/691 X |
| 4,155,638 | 5/1979 | Blitzer | 355/3 DD |
| 4,226,525 | 10/1980 | Sakamoto et al. | 355/14 D |
| 4,273,843 | 6/1981 | Fujita et al. | 355/3 DD |
| 4,306,804 | 12/1981 | Sakamoto et al. | 355/14 D |

FOREIGN PATENT DOCUMENTS 49-84031 7/1974 Japan .
52-129527 10/1977 Japan .
54-115240 9/1979 Japan .

Primary Examiner—Richard L. Moses
Attorney, Agent, or Firm—H. Fleischer; J. E. Beck; R. Zibelli

[57] ABSTRACT

An apparatus in which the developability of electrostatically charged particles in a mixture of particulate material is measured. The apparatus includes a transparent member positioned closely adjacent to a developer roller of an electrophotographic printing machine. Electrostatically charged particles are attracted from the particulate mixture being transported by the developer roller to the member. A beam of energy is transmitted through the member. The intensity of the internally reflected beam is detected and a signal generated indicative of the quantity of charged particles adhering to the member.

26 Claims, 10 Drawing Figures

AUTOMATIC DEVELOPABILITY SENSING IN ELECTROPHOTOGRAPHIC PRINTING

AUTOMATIC DEVELOPABILITY SENSING IN ELECTROPHOTOGRAPHIC PRINTING

This invention relates generally to an electrophotographic printing machine, and more particularly concerns an apparatus and method for sensing electrostatically charged particles in a mixture of particulate material.

Generally, the process of electrophotographic printing includes charging a photoconductive member to a substantially uniform potential so as to sensitize the surface thereof. The charged portion of the photoconductive surface is exposed to a light image of an original document being reproduced. This records an electrostatic latent image on the photoconductive member corresponding to the informational areas contained in the original document. After the electrostatic latent image is recorded on the photoconductive member, the latent image is developed by bringing a developer mixture into contact therewith. This forms a powder image on the photoconductive member which is subsequently transferred to a copy sheet. Finally, the powder image is heated to permanently affix it to the copy sheet in image configuration.

A common type of developer mixture frequently used in electrophotographic printing machines comprises carrier granules having toner particles adhering triboelectrically thereto. This two-component mixture is brought into contact with the photoconductive surface. The toner particles are attracted from the carrier granules to the latent image. During usage, toner particles are depleted from the developer mixture and must be periodically replenished therein. Heretofore, the concentration of toner particles in the developer mixture was controlled within a preselected bandwidth. However, in an electrophotographic printing machine, it is desirous to achieve optimum developability rather than merely maintaining the concentration of toner particles within the developer mixture at a substantially constant level. In order to optimize developability, the output density of the copy corresponds substantially to the input density of the original document. In order to achieve the foregoing, it is necessary to regulate the developability of the developer mixture. Developability is related to the environmental conditions such as temperature and humidity, as well as the concentration of tone particles in the developer mixture. Other physical parameters of the development system also affect developability, for example, spacing, electrical bias, mass flow rate, and the magnetic field pattern, amongst others. In addition, many other factors such as the state of compaction of the developer mixture, the charge on the toner particles and carrier granules as well as the state of attraction of toner particles to the carrier granules influence developability. Thus, in order to truly regulate developability so as to optimize the resultant copy, development of the latent image must be simulated.

Various techniques have been devised for measuring the concentration of toner particles within a developer mixture. The following disclosures appear to be relevant:

U.S. Pat. No. 3,341,411
Patentee: Harrick
Issued: Mar. 4, 1969

U.S. Pat. No. 3,460,893
Patentee: Wilks, Jr.
Issued: Aug. 12, 1969

U.S. Pat. No. 3,591,287
Patentee: Hannis
Issued: July 6, 1971

Japanese Patent Application No. 47-128270
Applicant: Canon, Inc.
Application Date: Nov. 7, 1972
Laid-Open No. 49-84031
Laid-Open Date: July 20, 1974

Japanese Patent Application No. 51-46163
Applicant: Canon, Inc.
Application Date: Apr. 23, 1976
Laid-Open No. 52-129527
Laid-Open Date: Oct. 31, 1977

Japanese Patent Application No. 53-22472
Applicant: Ricoh Company
Application Date: Feb. 28, 1978
Laid-Open No. 54-115240
Laid-Open Date: Sept. 7, 1979

The relevant portions of the foregoing disclosures may be briefly summarized as follows:

Harrick describes an infrared source generating a beam of infrared radiation through a light pipe. The beam of radiation is internally and multiply reflected from the surfaces of the light pipe. A light detector measures the intensity of the radiation transmitted through the light pipe. A powder is deposited on the surface of the light pipe. In this way, the absorption spectrum of the powder is recorded.

Wilks, Jr. discloses a hollow, cylindrical crystal having beveled edges. A source of radiant energy transmits a ray through the beveled edge at an angle greater than the critical angle. The ray passes into the annulus of crystal striking the internal surface thereof at an angle less than the critical angle. The rays are multiply reflected until emerging from the opposed beveled edge. A spectrophotometer receives the ray and produces a spectrum which is affected by the absorption of the material to be analyzed that lies in contact tangentially with the crystal.

Hannis describes the use of internal reflection of infrared radiation to measure samples of solids.

Canon ('270) describes a flat plate positioned so that the developer material on a magnetic brush contacts a flat area on the plate. Light rays are transmitted onto the flat area and reflected to a photodetector. In this way, the concentration of toner in the developer material is sensed.

Canon ('163) discloses a light permeable separation wall contacting developer material on a magnetic brush. The light permeable wall has an electrically conductive layer on its surface. Light rays are reflected from the wall to a photodetector. The reflected light is measured under two different states, i.e. when the electrical field attracts the toner and repels the toner.

Ricoh describes an equilateral triangle with the electrodes being made of a glass plate having an electrically conductive coating and two metal plates. The electrodes are insulated from one another with developer material passing within the triangle. A lamp is located at the apex of the metal plates with a pair of photodetectors being positioned on the other side of the glass plate. The plate is electrically biased with the polarity being alternately reversed. The detected signals are an indication of the performance capabilities of the developer material.

In accordance with one aspect of the present invention, there is provided an apparatus for sensing electrostatically charged particles. The apparatus includes a member adapted to attract at least a portion of the charged particles to at least one surface thereof. Means transmit a beam of energy through the member onto the charged particles attracted to the surface thereof. Means are provided for detecting the intensity of the beam of energy internally reflected through the member. The detecting means generates a signal indicative of the quantity of the charged particles attracted to the surface of the member.

Pursuant to another aspect of the present invention, there is provided an electrophotographic printing machine of the type having a developer roller for transporting a developer mixture comprising at least electrostatically charged particles closely adjacent to an electrostatic latent image recorded on a photoconductive surface so as to develop the latent image with the charged particles. The printing machine includes a member, positioned closely adjacent to the developer roller, adapted to attract at least a portion of the charged particles to at least one surface thereof. Means transmit a beam of energy through the member onto the charged particles attracted to the surface thereof. Means are provided for detecting the intensity of the beam of energy internally reflected through the member. The detecting means generates a signal indicative of the quantity of the charged particles attracted to the surface of the member.

Another aspect of the present invention comprises a method of sensing electrostatically charged particles. The method includes the steps of attracting at least a portion of the charged particles to at least one surface of the member. A beam of energy is transmitted through the member onto the charged particles attracted to the surface of the member. The intensity of the beam of energy internally reflected through the member is detected.

Still another aspect of the present invention comprises a method of electrophotographic printing in which a developer roller transports a developer mixture comprising at least electrostatically charged particles closely adjacent to an electrostatic latent image recorded on a photoconductive surface so as to develop the latent image with the charged particles. The method includes the steps of locating a member closely adjacent to the developer roller. At least a portion of the charged particles are attracted to at least one surface of the member. A beam of energy is transmitted through the member onto the charged particles attracted to the surface of the member. The intensity of the beam of energy internally reflected through the member is detected.

Other features of the present invention will become apparent as the following description proceeds and upon reference to the drawings, in which.

While the present invention will hereinafter be described in connection with various embodiments and methods of use, it will be understood that it is not intended to limit the invention to these embodiments and methods of use. On the contrary, it is intended to cover all alternatives, modifications and equivalents as may be included within the spirit and scope of the invention as defined by the appended claims.

Figure 1:
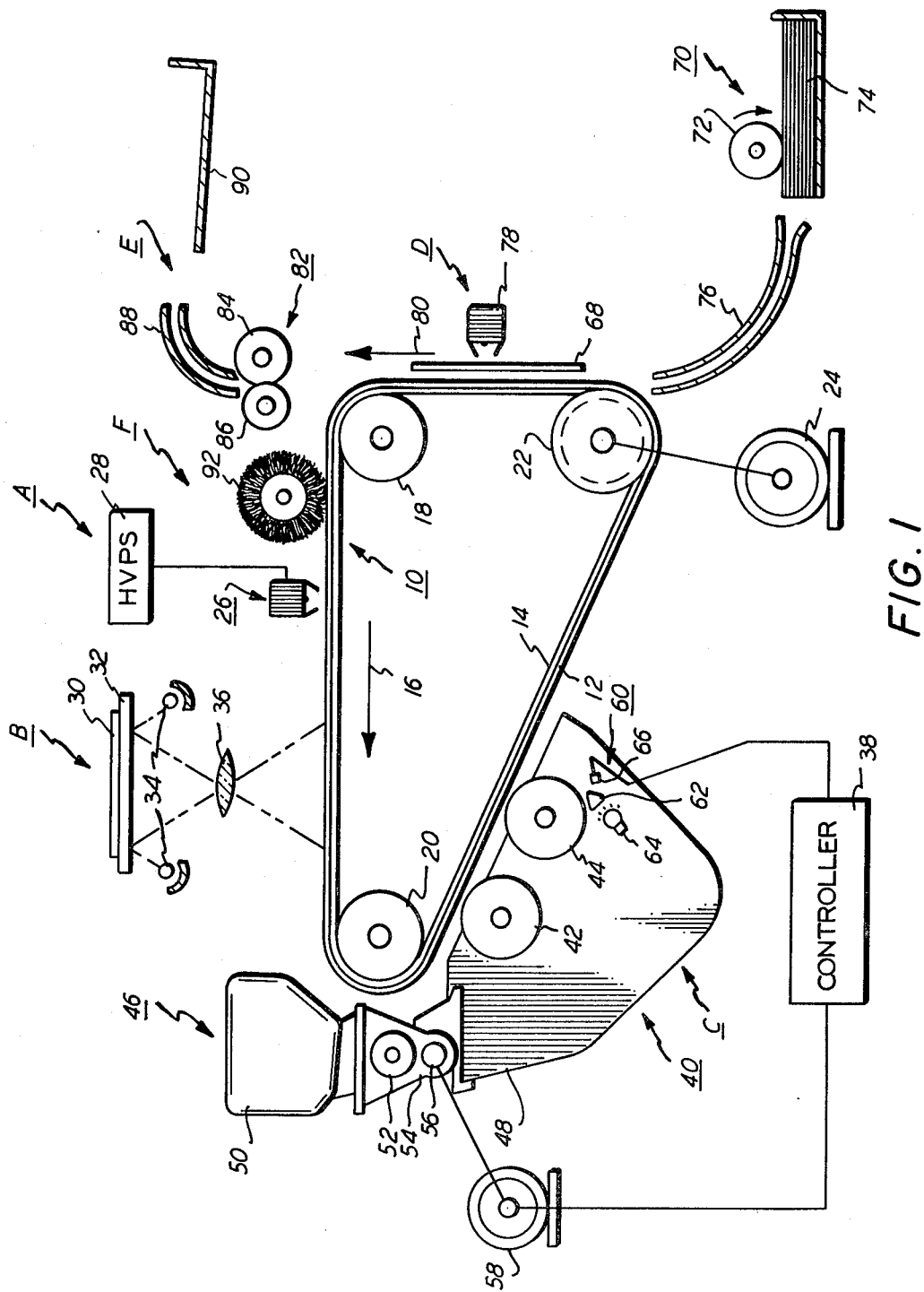
FIG. 1 is a schematic elevational view of an illustrative electrophotographic printing machine incorporating the apparatus of the present invention therein.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the features of the present invention therein. It will become apparent from the following discussion that the apparatus of the present invention is equally well suited for use in a wide variety of machines and is not necessarily limited in its application to the particular embodiment shown herein.

Inasmuch as the art of electrophotographic printing is well known, the various processing stations employed in the FIG. 1 printing machine will be shown hereinafter schematically and their operation described briefly with reference thereto.

Referring now to FIG. 1, the electrophotographic printing machine employs a belt 10 having a photoconductive surface 12 deposited on a conductive substrate 14. Preferably, photoconductive surface 12 is made from a selenium alloy. Conductive substrate 14 is made preferably from an aluminum alloy which is electrically grounded. Belt 10 moves in the direction of arrow 16 to advance successive portions of photoconductive surface 12 sequentially through the various processing stations disposed along the path of movement thereof. Belt 10 is entrained about stripping roller 18, tension roller 20 and drive roller 22. Drive roller 22 is mounted rotatably and in engagement with belt 10. Motor 24 rotates roller 22 to advance belt 10 in the direction of arrow 16. Roller 22 is coupled to motor 24 by a suitable means such as a belt drive. Drive roller 22 includes a pair of opposed, spaced edge guides. The edge guides define a space therebetween which determines the desired path of movement of belt 10. Belt 10 is maintained in tension by a pair of springs (not shown) resiliently urging tension roller 20 against belt 10 with the desired spring force. Both stripping roller 18 and tension roller 20 are mounted to rotate freely.

Initially, a portion of belt 10 passes through charging station A. At charging station A, a corona generating device, indicated generally by the reference numeral 26, charges photoconductive surface 12 to a relatively high, substantially uniform potential. High voltage power supply 28 is coupled to corona generating device 26. Excitation of power supply 28 causes corona generating device 26 to apply a charge on photoconductive surface 12 of belt 10.

After photoconductive surface 12 of belt 10 is charged, the charged portion thereof is advanced through exposure station B. At exposure station B, an original document is positioned facedown upon a transparent platen 32. Lamps 34 flash light rays onto original document 30. The light rays reflected from original document 30 are transmitted through lens 36 forming a light image thereof. Lens 36 focuses the light image onto the charged portion of photoconductive surface 12 to selectively dissipate the charge thereon. This records an electrostatic latent image on photoconductive surface 12 which corresponds to the informational areas contained within original document 30.

After the electrostatic latent image has been recorded on photo-conductive surface 12, belt 10 advances the latent image to development station C. At development station C, a magnetic brush development system, indicated generally by the reference numeral 40, advances developer material into contact with the latent image. Preferably, magnetic brush development system 40 includes two magnetic brush developer rollers 42 and 44. Each roller advances developer material into contact with the latent image. These developer rollers form a brush of carrier granules and toner particles extending outwardly therefrom. The latent image attracts toner particles from the carrier granules forming a toner powder image on the latent image. Preferably, the developer material is electrically conductive. As successive electrostatic latent images are developed, toner particles are depleted from the developer material. A toner particle dispenser, indicated generally by the reference numeral 46, includes a container 50 storing a supply of toner particles therein. Foam roller 52, disposed in a sump 54 beneath container 50, meters toner particles into auger 56. Motor 58 is coupled to auger 56. As motor 58 rotates, auger 56 advances toner particles for discharge into developer housing 48. Energization of motor 58 is regulated by controller 38. A sensor, indicated generally by the reference numeral 60 is positioned closely adjacent to developer roller 44. Sensor 60 comprises a substantially transparent prism 62 adapted to attract toner particles from the developer material adhering to developer roller 44. A light source 64 transmits light rays through prism 62 onto the toner particles adhering thereto. Light rays internally reflected through prism 62 are detected by light detector 66. Light detector 66 develops an electrical output signal which is transmitted to controller 38. Controller 38 develops an error signal which actuates motor 58 to dispense toner particles into developer housing 48. Thus, when the quantity of toner particles adhering to prism 66 is beneath a predetermined level, controller 38 actuates motor 58 to dispense additional toner particles into the developer material. The dispensing of additional toner particles into the developer material adjusts the developability of the system to the desired level. One skilled in the art will appreciate that sensor 60 may be disposed adjacent developer roller 42 in lieu of roller 44. The detailed structure of sensor 60 will be described hereinafter with reference to FIGS. 2 through 6, inclusive.

After the electrostatic latent image is developed, belt 10 advances the toner powder image to transfer station D. A sheet of support material 68 is advanced to transfer station D by sheet feeding apparatus 70. Preferably, sheet feeding apparatus 70 includes a feed roll 72 contacting the uppermost sheet of stack 74. Feed roll 72 rotates to advance the uppermost sheet from stack 74 into chute 76. Chute 76 directs the advancing sheet of support material into contact with photoconductive surface 12 of belt 10 in a timed sequence so that the toner powder image developed thereon contacts the advancing sheet of support material at transfer station D. Transfer station D includes a corona generating device 78 which sprays ions onto the back side of sheet 68. This attracts the toner powder image from the photoconductive surface 12 to sheet 68. After transfer, sheet 68 continues to move in the direction of arrow 80 onto a conveyor (not shown) which advances sheet 68 to fusing station E.

Fusing station E includes a fuser assembly, indicated generally by the reference numeral 82, which permanently affixes the transferred powder image to sheet 68. Preferably, fuser assembly 82 comprises a heated fuser roller 84 and back-up roller 86. Sheet 68 passes between fuser roller and back-up roller 86 with the toner powder image contacting fuser roller 84. In this manner, the toner powder image is permanently affixed to sheet 68. After fusing, chute 88 advances sheet 68 to catch tray 90 for subsequent removal from the printing machine by the operator.

After the sheet of support material is separated from photoconductive surface 12 of belt 10, the residual toner particles adhering to photoconductive surface 12 are removed therefrom at cleaning station F. Cleaning station F includes a rotatably mounted fibrous brush 92 in contact with photoconductive surface 12. The particles are cleaned from photoconductive surface 12 by the rotation of brush 92 in contact therewith. Subsequent to cleaning, a discharge lamp (not shown) floods photoconductive surface 12 with light to dissipate any residual electrostatic charge remaining thereon prior to the charging thereof for the next successive imaging cycle.

It is believed that the foregoing description is sufficient for purposes of the present invention to illustrate the general operation of an electrophotographic printing machine incorporating the features of the present invention therein.

Figure 2:
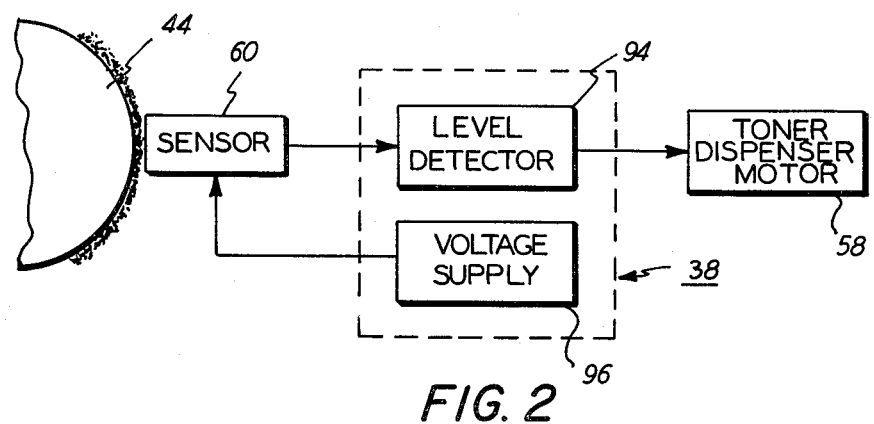
FIG. 2 is a block diagram of a control system used to regulate the developability of the developer mixture employed in the FIG. 1 printing machine.

As illustrated in FIG. 2, sensor 60 is disposed closely adjacent to developer roller 44. As developer roller 44 transports developer material into contact with the latent image recorded on photoconductive surface 12, sensor 60 is also developed with toner particles. The quantity of toner particles is detected and an electrical output signal generated indicative thereof. Controller 38 receives the electrical output signal from sensor 60 and processes it. Controller 38 includes a level detector 94 and a voltage supply 96. The voltage supply 96 is coupled to sensor 60 so as to furnish the appropriate electrical bias to the conductive surface adhering to the prism, and to the light source and light detector. By way of example, level detector 94 includes logic elements to process the electrical output signal from sensor 60. The logic elements, include preferably a suitable discriminator circuit for comparing a reference with the electrical output signal from sensor 60. The discriminator circuit may utilize a silicone control switch which turns on and effectively locks in after an electrical output signal has been obtained having a magnitude greater than the reference level (i.e. set point). The signal from the discriminator circuit changes the state of a flip-flop to develop an output signal therefrom. The output signal from the flip-flop, in conjunction with an output signal from the developer unit actuates an AND gate which, in turn, transmits a control signal to toner dispenser motor 58. The control signal also resets the flip-flop. This type of logic circuit is on-off. However, in the alternative, it is possible to utilize proportional circuitry which varies the quantity of toner particles metered to the developer unit as a function of the control signal. This may be achieved by a suitable integrated circuit module for developing a stepped proportional dispensing signal.

Figure 3:
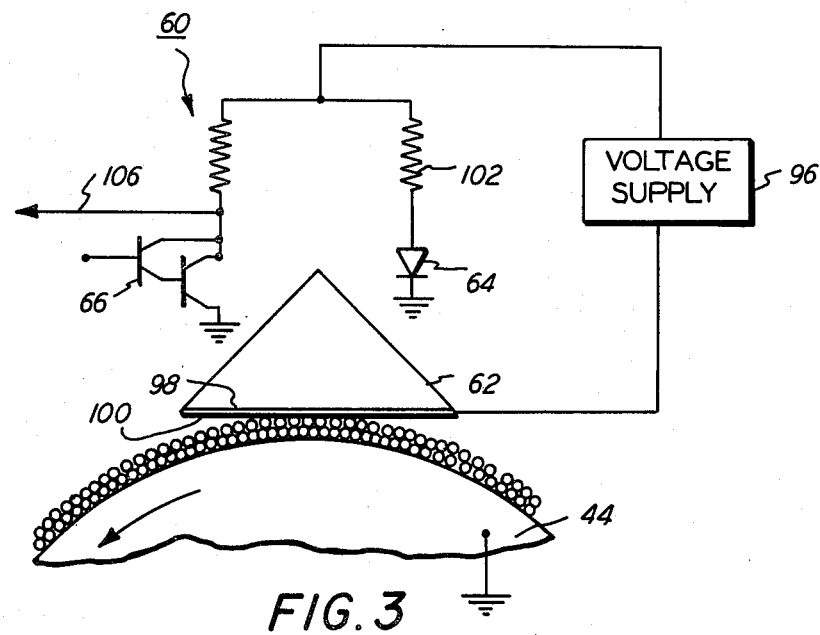
FIG. 3 is a schematic elevational view of the sensing circuitry associated therewith in the FIG. 2 control system.

Referring now to FIG. 3, prism 62 is preferably a right triangular prism with the hypotenuse, i.e. surface 98, having a substantially transparent electrically conductive layer 100 adhering thereto. Preferably, electrically conductive layer 100 is a transparent tin oxide coating which is made by Pittsburgh Plate Glass under the trademark NESA or is made by the Corning Glass Company under the trademark Electroconductive. The angles of transparent prism 62 opposed from the legs are equal and 45°. Voltage source 96 is coupled to electrically conductive layer 100 so as to electrically bias the surface of prism 62, thereby attracting toner particles being transported on developer roller 44 thereto. Light source 64 is preferably a light emitting diode with light detector 66 being a phototransistor. Light emitting diode 64 is coupled to voltage source 96 by resistor 102. Similarly, phototransistor 66 is coupled to voltage source 96 by resistor 104. Preferably, resistor 102 is about 560 ohms with resistor 104 being about 2200 ohms. The voltage applied across resistor 104 and phototransistor 66, which is connected in parallel with light emitting diode 64 and resistor 102 is preferably about 6 volts D.C.. Line 106 transmits the electrical output signal from phototransistor 66 to level detector 64 (FIG. 2).

In operation, phototransistor 62 senses the changes in internal reflectance from the surface on which the toner particles are developed. By Snell's law, internal reflectance occurs up to a critical angle. The critical angle is measured with respect to the normal surface. The value of the critical angle, $\theta_c$, is determined by the relationship since $\theta_c = N_1/N_2$, with $N_1$ and $N_2$ being the indices of refraction of the material in contact with the surface and the optical element respectively. Inasmuch as the presence of toner particles on the surface replaces air, the index of refraction is greater than 1. Thus, the critical angle is greater than the critical angle in the absence of toner particles on the surface. As toner particle deposition occurs on the surface, the critical angle increases and the magnitude of the internally reflected light detected is reduced. By way of example, the critical angle, without particles, is about 41.5° when the index of refraction of theprism is about 1.52.

It is believed that this system operates by detecting the intensity of radiation internally reflected from the hypotenuse of the right angle prism. The presence of toner particles on the prism face causes a decrease in the detected light intensity which corresponds to a decrease in the effective internal reflectivity of the surface. The total "internal" reflected radiation field extends beyond the prism face a distance on the order of a wavelength of light. This is the exponentially decaying evanescent field. Thus, there are two categories of energy coupling from the prism, one due to the intimate contact of the toner particles with the prism surface and another due to the toner particles located near the prism surface mediated by the evanescent field. In the first case, the internal reflectivity of the prism surface is reduced by transmission into the toner particles, characterized by an index of refraction and an absorption coefficient. The second operates by evanescent field coupling of energy from the prism surface to the toner particles rather than relying on intimate contact between the surface and the toner particles. It appears that the evanescent field effect dominates to produce the large signal sensitivity that has been found in this sensing apparatus.

Figure 4:
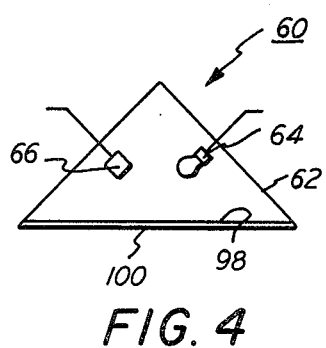
FIG. 4 is a schematic elevational view showing a preferred embodiment of the prism, light source and light sensor of the FIG. 3 sensor.

Referring now to FIG. 4, there is shown an embodiment of sensor 60 wherein phototransistor 66 and light emitting diode 64 are embedded in prism 62. As illustrated thereat, phototransistor 66 is embedded in prism 62 adjacent a surface thereof opposed from one of the 45° angles, i.e. one leg. Similarly, light emitting diode 64 is embedded in prism 62 adjacent the other surface thereof opposed from the other 45° angle, i.e. the other leg. Preferably, the internal angle of incidence of the light source is slightly greater than the critical angle, i.e. greater than 41.5°. In this way, the light rays internally reflected from the toner particles adhering to electrically conductive layer 100 on surface 98 are detected by phototransistor 66 such that the output signal therefrom is maximized. It should also be noted that not only may visible light rays be employed, but longer wavelength radiation such as an infrared light source may also be utilized in this system.

Figure 5:
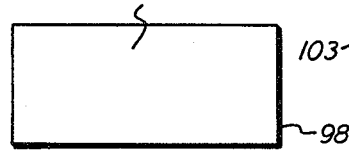
FIG. 5 is a schematic plan view of the FIG. 4 prism depicting one embodiment of the pattern of conductive material adhering to a surface of the prism.

Turning now to FIG. 5, there is shown one embodiment of the transparent electrically conductive layer adhering to surface 98 of prism 62. As depicted thereat, electrically conductive layer 100 covers the entire surface of surface 98 and is substantially uniform. An electrically conductive layer of this type maximizes simulation of solid area development. In developing electrostatic latent images on a photoconductive surface, both the solid areas and lines must be developed. Thus, if one wishes to simulate the solid areas within the electrostatic latent image, layer 100 would be substantially uniform on surface 98.

Figure 6:
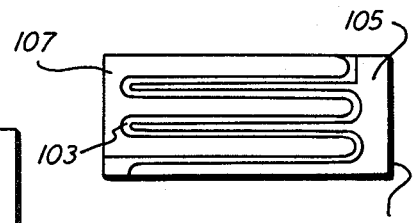
FIG. 6 is a schematic plan view of the FIG. 4 prism depicting another embodiment of the pattern of conductive material adhering to a surface of the prism.

Referring now to FIG. 6, an alternate embodiment of the electrically conductive layer 100 adhering to surface 98 is depicted thereat. As illustrated in FIG. 6, electrically conductive layer 100 only covers discrete portions or regions of surface 98 with the other regions being nonconductive. Thus, electrically conductive layer 100 forms a plurality of interdigitated conductive regions with the regions adjacent thereto being nonelectrically conductive. A surface coating of this type will optimize simulation of lines in the electrostatic latent image being developed. Hence, as shown in FIG. 6, non-conductive region 103 is adjacent to conductive regions 105 and 107. The toner particles will only be attracted to conductive regions so as to simulate line development in the electrostatic latent image. When conductive regions 105 and 107 are electrically biased to different potentials, line development is simulated. Alternatively, if conductive regions 105 and 107 are electrically biased to the same potential, solid area development is simulated. Non-conductive region 103 is formed by etching the pattern of conductive regions 105 and 107 on surface 98.

Figure 7:
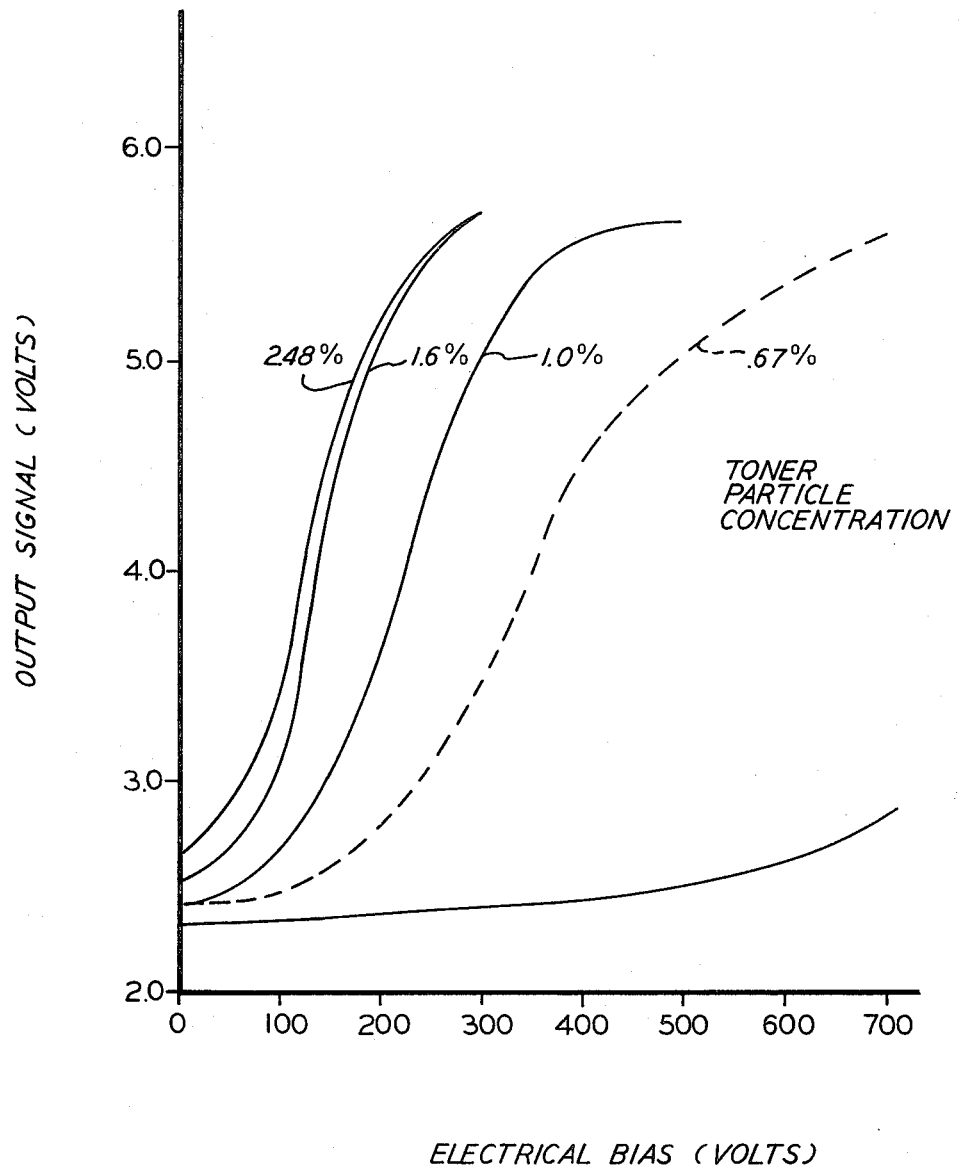
FIG. 7 is a graph illustrating a set of developability curves.

Referring now to FIG. 7, there is shown a plurality of curves with each curve corresponding to a different toner particle concentration within the developer mixture. These curves are plotted as a function of output signal versus electrical bias applied to the electrically conductive layer adhering to the surface of the prism. Thus, FIG. 7 represents a set of developability curves. Each developability curve was generated by step-wise increasing of the bias from 0 volts and subsequently decreasing step-wise with the plotted values representing the averages of each bias voltage. It was found that the discrepancy between increasing and decreasing bias data was less than 5% for the 1% toner concentration curve. It should be noted that the output signal includes the non-linearity due to saturation of the phototransistor sensing arrangement at high levels of toner deposition, i.e. the reduced internal reflectance on the electrically conductive surface coated with toner particles. These curves, as shown in FIG. 7, appear to be very similar to the typical developability curves.

Figure 8:
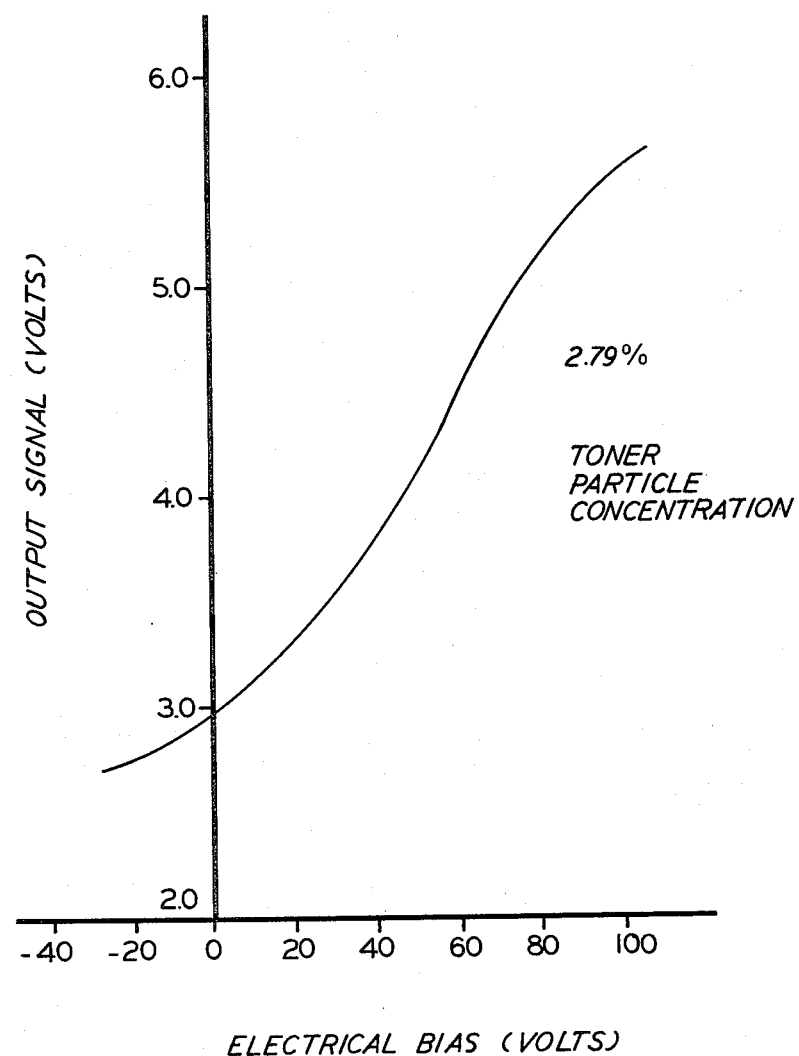
FIG. 8 is a graph showing developability information in the region of low electrical bias.

Turning now to FIG. 8, there is shown, for both positive and negative electrical biases, the output signal for a developer material having a toner concentration of 2.79%. This curve illustrates that developability information may be found in the low electrical bias, i.e. toe region thereof. Data was taken in 10 volt bias increments on either side of 0 volts in the toe region.

Figure 9:
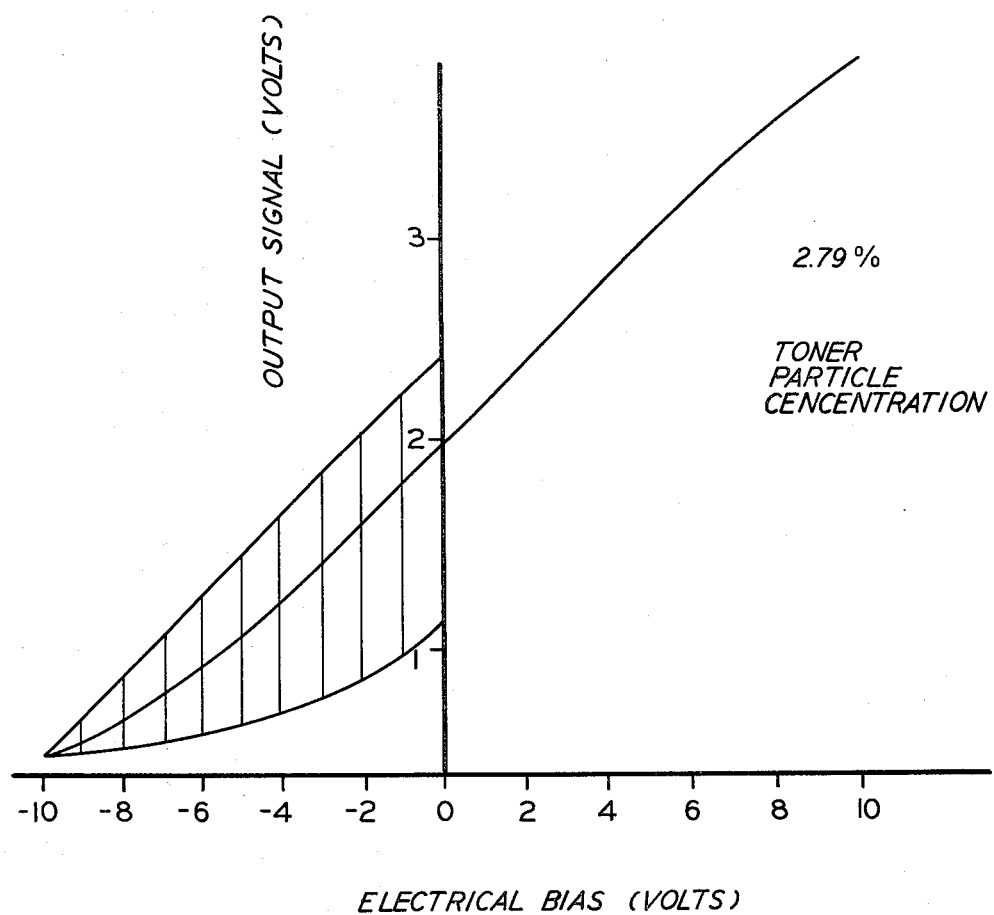
FIG. 9 is a graph depicting the historysis in developability information in the low electrical bias region.

Referring now to FIG. 9, there is shown a further expansion of the developability curves in the toe region for the developer material of FIG. 8. Here, the developability information was taken in 1 volt biasing increments on either side of 0 volts in the toe region. Error bars are included in this figure showing the increasing and decreasing curve data points which show appreciable spread, particularly in the negative bias region. With small, i.e. 1 volt steps, the rate at which the toner deposition approaches its new equalibrium is appreciably slower giving rise to a time dependent historysis effect.

Figure 10:
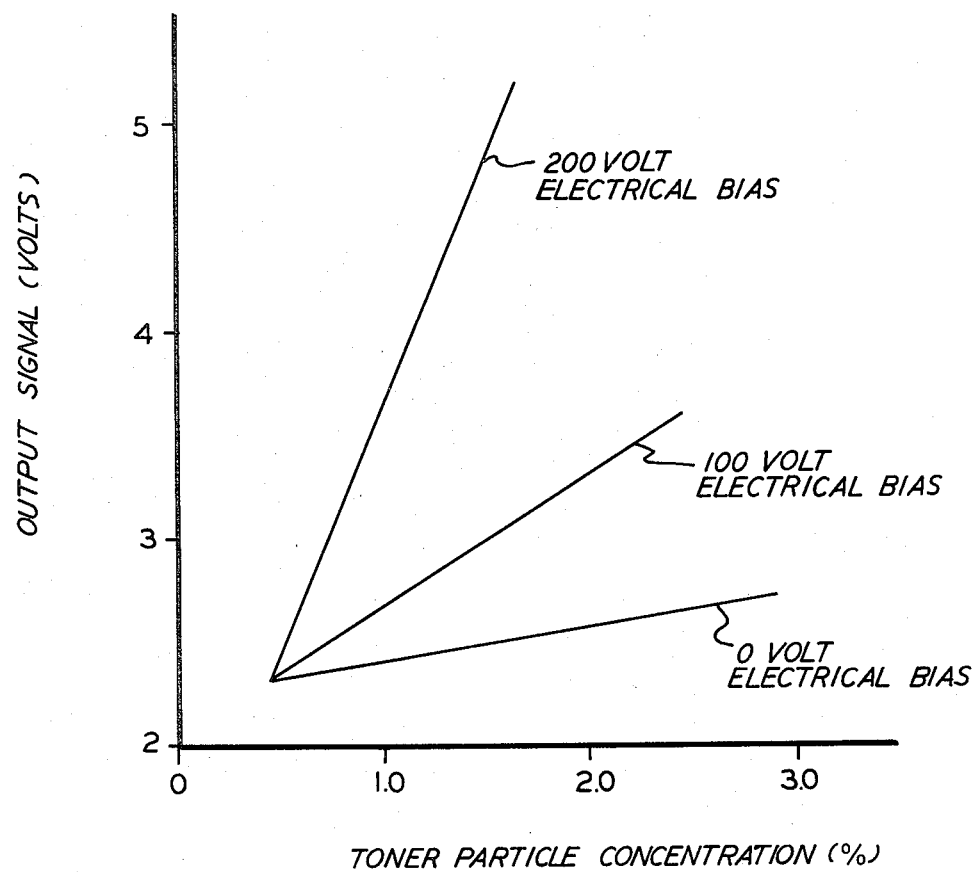
FIG. 10 is a graph illustrating developability information for various electrical biases.

Turning now to FIG. 10, there is shown a graph of toner particle concentration as a function of electrical output signal for various biases applied to the electrically conductive layer adhering to the surface of the prism. This represents a simple control strategy for furnishing additional toner particles to the system. As shown, for a fixed electrical bias applied to the electrically conductive layer adhering to the surface of the prism, the electrical output signal increases as the toner concentration within the developer material increases. This signal, which is a measure of the toner particle concentration, is transmitted to the controller for energizing the toner dispenser motor to maintain the toner particle concentration at the desired level.

The availability of detailed developability information from the sensing apparatus of the present invention enables the system to furnish additional toner particles to the developer material as a function of the developability curve. In addition, this information is useful, not only controlling the concentration of toner particles within the developer material, but also for regulating the electrical bias applied to the developer roller. The detailed developability curve information may be employed for the addition of two different types of toner particles or toner particles plus an additive to the developer material. Furthermore, the level of charge applied to the photoconductive surface during charging may also be controlled as a function of this information.

It is thus clear that the sensing apparatus of the present invention simulates developability within an electrophotographic printing machine to optimize control of development. Furthermore, the system not only provides a means for controlling the concentration of toner particles within the developer material, but may also provide a technique for regulating charging and the electrical bias applied to the developer roller, as well. The utilization of this control scheme optimizes various parameters within the printing machine to automatically account for varying environmental and aging characteristics. Hence, the sensing apparatus of the present invention provides a means whereby significant improvements may be achieved in the quality of copies produced by electrophotographic printing machines.

In recapitulation, it is apparent that the sensing apparatus of the present invention measures the change in internal reflectance to provide a signal indicative of developability. This signal may be employed to control the concentration of toner particles within the developer material, adjust charging and regulate the electrical bias applied to the developer roller, amongst others.

It is, therefore, apparent that there has been provided, in accordance with the present invention, an apparatus for sensing developability in an electrophotographic printing machine. This apparatus fully satisfies the aims and advantages hereinbefore set forth. While this invention has been described in conjunction with specific embodiments and methods of use, it is evident that many alternatives, modifications and variations will be apparent to those skilled in the art. Accordingly, it is intended to embrace all such alternatives, modifications and variations as fall within the spirit and broad scope of the appended claims.

What is claimed is:

1. An apparatus for sensing electrostatically charged particles, including:
    a member adapted to attract at least a portion of the charged particles to at least one surface thereof;
    means for transmitting a beam of energy through said member onto the charged particles attracted to the surface thereof with the internal angle of incidence of the beam of energy being greater than the critical angle of incidence of said member; and
    means for detecting the intensity of the beam of energy internally reflected through said member, said detecting means generating a signal indicative of the quantity of charged particles attracted to the surface of said member.

2. An apparatus according to claim 1, wherein said member includes:
    a substantially transparent prism; and
    a substantially transparent, electrically conductive layer adhering to one surface of said prism.

3. An apparatus according to claim 2, wherein said member includes means for electrically biasing said conductive layer to attract the charged particles thereto.

4. An apparatus for sensing electrostatically charged particles, including:
    a substantially transparent, right triangular prism having equal opposed interior angles;
    a substantially transparent, electrically conductive layer adhering to one surface of said prism;
    means for electrically biasing said conductive layer to attract the charged particles thereto;
    means for transmitting a beam of energy through said prism onto the charged particles attracted to said conductive layer; and
    means for detecting the intensity of the beam of energy internally reflected through said prism, said detecting means generating a signal indicative of the quantity of charged particles attracted to the surface of said conductive layer.

5. An apparatus according to claim 4, wherein said conductive layer adheres to the surface of said prism opposed from the right angle thereof.

6. An apparatus according to claim 5, wherein said transmitting means includes a light source transmitting light rays through said prism and said conductive layer onto the charged particles adhering thereto.

7. An apparatus according to claim 6, wherein said light source is secured to a surface of said prism other than the surface of said prism having said conductive layer adhering thereto.

8. An apparatus according to claim 6, wherein said detecting means includes a light sensor positioned to receive light rays internally reflected through said prism.

9. An apparatus according to claim 8, wherein said light sensor is secured to a surface of said prism.

10. An apparatus according to claim 8, wherein said conductive layer is a substantially uniform area adhering to the surface of said prism.

11. An apparatus according to claim 8, wherein the surface of said prism having said conductive layer adhering thereto is arranged in a pattern of conductive and non-conductive regions.

12. An apparatus according to claim 9, wherein said light source is a light emitting diode.

13. An apparatus according to claim 12, wherein said light sensor is a phototransistor.

14. An electrophotographic printing machine of the type having a developer roller for transporting a developer mixture comprising at least electrostatically charged particles closely adjacent to an electrostatic latent image recorded on a photoconductive surface so as to develop the latent image with the charged particles, wherein the improvement includes:
a member, positioned closely adjacent to the developer roller, adapted to attract at least a portion of the charged particles to at least one surface thereof;
means for transmitting a beam of energy through said member onto the charged particles attracted to the surface thereof, with the internal angle of incidence of the beam of energy being greater than the critical angle of incidence of said member;
means for detecting the intensity of the beam of energy internally reflected through said member, said detecting means generating a signal indicative of the quantity of charged particles attracted to the surface of said member; and
means, responsive to the signal generated by said detecting means, for controlling the concentration of charged particles in the developer mixture.

15. A printing machine according to claim 14, wherein said member includes:
a substantially transparent prism; and
a substantially transparent, electrically conductive layer adhering to one surface thereof.

16. A printing machine according to claim 15, wherein said member includes means for electrically biasing said conductive layer to attract the charged particles thereto.

17. An electrophotographic printing machine of the type having a developer roller for transporting a developer mixture comprising at least electrostatically charged particles closely adjacent to an electrostatic latent image recorded on a photoconductive surface so as to develop the latent image with the charged particles, wherein the improvement includes:
a substantially transparent, right triangular prism having equal opposed interior angles, said prism being positioned closely adjacent to the developer roller;
a substantially transparent, electrically conductive layer adhering to one surface of said prism opposed from the developer roller;
means for electrically biasing said conductive layer to attract the charged particles thereto;
means for transmitting a beam of energy through said prism onto the charged particles attracted to said conductive layer; and
means for detecting the intensity of the beam of energy internally reflected through said prism, said detecting means generating a signal indicative of the quantity of charged particles attracted to the surface of said conductive layer.

18. A printing machine according to claim 17, wherein said conductive layer adheres to the surface of said prism opposed from the right angle thereof.

19. A printing machine according to claim 18, wherein said transmitting means includes a light source transmitting light rays through said prism and said conductive layer onto the charged particles adhering thereto.

20. A printing machine according to claim 19, wherein said light source is secured to a surface of said prism other than the surface of said prism having said conductive layer adhering thereto.

21. A printing machine according to claim 19, wherein said detecting means includes a light sensor positioned to receive light rays internally reflected through said prism.

22. A printing machine according to claim 21, wherein said light sensor is secured to a surface of said prism.

23. A printing machine according to claim 21, wherein said conductive layer is a substantially uniform area adhering to the surface of said prism.

24. A printing machine according to claim 21, wherein the surface of said prism having said conductive layer adhering thereto is arranged in a pattern of conductive and non-conductive regions.

25. A printing machine according to claim 22, wherein said light source is a light emitting diode.

26. A printing machine according to claim 25, wherein said light sensor is a phototransistor.

* * * * *